United States Patent [19]

Linkow

[11] Patent Number: 5,116,226
[45] Date of Patent: * May 26, 1992

[54] NECKLESS BLADE IMPLANT

[76] Inventor: Leonard I. Linkow, 1530 Palisades Ave., Fort Lee, N.J. 07024

[*] Notice: The portion of the term of this patent subsequent to May 5, 2009 has been disclaimed.

[21] Appl. No.: 592,963

[22] Filed: Oct. 4, 1990

Related U.S. Application Data

[63] Continuation-in-part of Ser. No. 252,290, Sep. 30, 1988.

[51] Int. Cl.⁵ .............................................. A61C 8/00
[52] U.S. Cl. ................................................... 433/176
[58] Field of Search ................................ 433/176, 173

[56] References Cited

U.S. PATENT DOCUMENTS

| | | |
|---|---|---|
| 3,683,501 | 8/1972 | Edelman ............................ 433/176 |
| 3,992,780 | 11/1976 | Herskovits ......................... 433/176 |
| 4,024,638 | 5/1977 | Linkow et al. ..................... 433/176 |
| 4,081,908 | 4/1978 | Sneer ................................. 433/176 |
| 4,109,382 | 8/1978 | Koch ............................... 433/176 X |
| 4,179,810 | 12/1979 | Kirsch ............................ 433/176 X |
| 4,531,917 | 7/1985 | Linkow et al. ..................... 433/176 |
| 4,573,922 | 3/1986 | Bello ................................. 433/176 |
| 4,600,388 | 7/1986 | Linkow ............................. 433/176 |
| 4,661,066 | 4/1987 | Linkow et al. ..................... 433/176 |
| 4,762,492 | 8/1988 | Nagai ............................. 433/176 X |
| 4,799,886 | 1/1989 | Wimmer ........................... 433/176 |
| 4,997,383 | 3/1991 | Weiss et al. ...................... 433/176 |

FOREIGN PATENT DOCUMENTS

| | | | |
|---|---|---|---|
| 2632853 | 12/1989 | France ............................. 433/176 |
| 2193640 | 2/1988 | United Kingdom ............... 433/176 |

Primary Examiner—Robert P. Swiatek
Assistant Examiner—Nicholas D. Lucchesi
Attorney, Agent, or Firm—Darby & Darby

[57] ABSTRACT

An oral implant for supporting an artificial tooth structure has a generally triangularly shaped implant portion adapted to be fitted in an opening in a bone in the vicinity of the occlusal plane of a patient in such a manner that at least a part of the connection part extends beyond a rim of the opening in the bone or can remain just below the bone while the base of the post rests on the bone. There is at least one post portion having first and second ends. The first end is adapted to receive at least a part of the artificial tooth structure. The second end is adapted for a direct connection to the connection part of the implant portion. The implant portion has mesial and distal occlusional struts extending from the sides of the implant portion. The struts are directed toward a plane perpendicular to the apex of the triangle and end in the bucco-lingual cortice of bone.

25 Claims, 3 Drawing Sheets

NECKLESS BLADE IMPLANT

This is a continuation-in-part of Leonard Linkow's U.S. patent application Ser. No. 252,290 filed on Sep. 30, 1988, now pending.

BACKGROUND OF THE INVENTION

This invention relates to dental implants and, more particularly, to neckless blade implants.

A dental implant, such as that described in U.S. Pat. Nos. 3,465,441 and 3,660,899 of the present inventor are used to support an artificial bridge, tooth or other dental prosthesis. The implant has an implant portion, e.g. in the form of a blade, that is secured in the underlying bone in an edentulous span. A post portion, typically with a recessed neck part, extends up form the implant portion and supports the artificial bridge or crown. This type implant is inserted by making an incision in the fibromucosal tissue down to the underlying alveolar ridge crest bone. The tissue is then reflected to expose the bone and a burr is used to create a groove in the bone which is as deep as the implant portion. The implant portion is then wedged into the bone. After the insertion, the tissue is sutured about the neck part so that the rest of the post protrudes above the tissue line. Typically, a few weeks or months are allowed to pass before the dental prosthesis is attached to the post. During this period, bone starts to grow around the implant portion and through holes provided in it, thereby acting to anchor the implant in place before it is stressed by use.

Submergible blade implants, such as that shown in U.S. Pat. No. 4,177,562 of A. L. Miller and A. J. Viscido, allow a blade to be inserted in the jawbone for a long period of time before being placed in actual use. With this type of implant the blade is completely submerged in the bone. It is then covered over and allowed to remain in place for several months. For this period it is protected against being dislodged by the tongue or other teeth during mastication. Once there has been substantial regrowth of the bone over, around and through the submerged blade, the tissue is again opened and the post is attached to the blade by a typical screw connection.

As noted, it is common for many types of oral implants disclosed by the prior art to have a post with a neck portion which connects to a blade. Such a neck portion is typically much narrower than the rest of the post and the blade. In view of that, a step-type transitioned area is defined between the post and the blade. Steep variation between the dimensions of the blade, post and the neck makes the transitioned area subject to a much greater concentration of the stresses than other areas of the implant. All this makes the design of the narrow neck the weak spot of the oral implants disclosed by the prior art. In use, such implants can bend in the area of the neck portion when chewing movements are performed. This might cause bone resorption immediately below the neck portion and cause the neck to break.

U.S. Pat. No. 4,178,686 to Riess et al. provides an oral implant in which the implant portion is a polymer matrix having spherical particles of tricalciumphosphate ceramic embedded in its exterior. A post portion has an elongated core member extending substantially into the implant portion. The base of the top part of the post portion extends to the outer edges of the implant portion and tapers inward in the part towards the artificial tooth support. The tooth support itself may be attached to the post by means of a threaded shaft. With this arrangement, the forces of mastication are resisted solely by the threaded shaft, which is relatively narrow, and/or the narrow core portion of the post.

The present inventor's own U.S. Pat. No. 4,600,388 discloses a blade in which the post is designed to straddle recessed portions in the blade. Because of these recessed portions in the blade, the post does not extend beyond the outer limits of the blade. Further, the legs of the implant, that allow it to straddle the blade, are relatively thin and these thin legs must resist the forces of mastication. Further, there is no direct means for rigidly securing the post to the blade, other than the nature spring force of the legs of the post.

The relatively narrow neck portions of posts in prior art implants are subject to bending and breakage during normal use. When this occurs it is often necessary to remove part or all of the implant, including the blade portion, to repair the damage. Thus, it would be extremely advantageous if blade implants could be provided with extremely rugged post portions which could easily resist the forces of mastication.

SUMMARY OF THE INVENTION

The present invention provides an oral blade-type implant for supporting an artificial tooth structure in which (a) the traditional recessed neck portion of the support post is eliminated, and (b) one end of the post is adapted for a direct connection to the blade and has a width and length such that the post base extends outwardly from sides of the blade, thus defining shoulders for support of the artificial dental structure.

In an illustrative embodiment of the invention, the oral implant for supporting an artificial tooth structure includes an implant portion in the form of a blade. This blade is adapted to be fitted in an opening in the patient's mandible or maxilla in the vicinity of the occlusal plane. On the edge of the blade directed toward the occlusal plane, the blade has at least one connection part that projects toward the occlusal plane. The installation of the blade in the bone is such that at least a portion of the connection part extends out of the bone. At least one post portion is adapted to receive at least a part of the artificial tooth structure at the end and is directly connected to the connection part of the implant portion at its base or other end. The post has a size at its base such that it extends outwardly from sides of the connection part, defining shoulders for supporting the artificial tooth structure.

In a preferred embodiment the implant portion has a substantially triangular configuration. The connection portion of the implant part is positioned at one angle of the triangle and the shoulders of the base of the post extend outwardly from the sides of the triangle. The shoulders of the base of the post overlap surfaces of the connection part of the implant portion in the bucco-lingual direction. Also the shoulders may extend from the connection part of the implant portion in the bucco-lingual direction. A cross-section of the implant portion in the bucco-lingual direction can have a wedge-shaped configuration with wide and narrow sides. The wide side in this arrangement is connected to the base of the post portion.

In another embodiment the implant portion has a bending arrangement to enable the oral implant to be bent in the mesio-distal direction. The bending arrangement is achieved with a pair of V-shaped slits. one on each side of the connection part.

In a still further embodiment the post portion is detachably connected to the implant portion and the second or base end of the post portion is adapted to straddle the connection part of the implant portion. The base of the post portion has a pair of spaced apart legs and the connection part of the implant portion has a pair of recesses. In the assembled condition of the oral implant the legs fit within the recesses of the implant portion.

In yet another embodiment the implant portion has upwardly directed struts towards both ends. These struts end about 2 mm below the level of the mounting post. At least a portion of these struts will lie in cortical bone, which is the bone closest to the gums. Cortical bone is stronger than the medullary bone which lies deeper in the jaw. This implant is more firmly anchored in the jaw because of the additional portion surrounded by the cortical bone.

In yet a further embodiment, the triangular implant portion has a cut-out portion which exposes the threads of a screw-type post portion. The bone adheres to the threads for a strong, permanent bond in the jaw. A coronal ring and/or an apical disc may be included to guide the screw-type post portion in the threaded implant.

It still another embodiment, the triangular implant portion has a recess along the upper surface extending toward the opposite surface of the implant portion.

BRIEF DESCRIPTION OF THE DRAWINGS

Other advantages and features of the invention are described with reference to exemplary embodiments, which are intended to explain and not to limit the invention. and are illustrated in the drawings in which.

DESCRIPTION OF ILLUSTRATIVE EMBODIMENT

Although a specific embodiment of the invention will now be described with reference to the drawings. it should be understood that the embodiment shown is by way of example only and merely illustrative of but one of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

Figure 1:
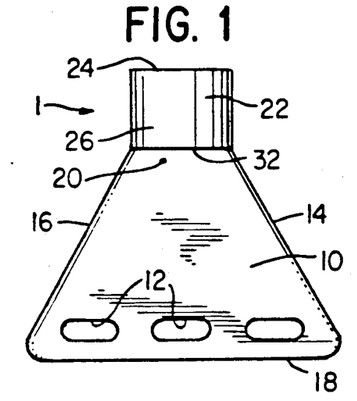
FIG. 1 is a view of a dental implant according to the present invention.

In FIG. 1 there is shown an enlarged embodiment of the invention. An oral implant 1 includes an implant portion in the form of a blade 10 and a post portion 22. In the embodiment of FIG. 1, the blade and the post are permanently attached to each other.

The blade 10 has holes or vents 12 which allow bone to grow completely through the blade so as to anchor the implant in place.

It is shown in FIG. 1 that the blade in the mesio-distal plane has a substantially triangular configuration with rounded off angle portions. However, other configurations of the plate are possible. The triangular blade 10 has sides 14 and 16 and a base 18. The width of the base 18 should be such as to allow tight engagement with an opening in a bone in which the implant is inserted.

A connection part 20 is located at the apex of the triangular plate i.e. opposite the base 18. A post portion 22 having a first end 24 and a second or base end 26 is attached to the connection part 20. The first end 24 receives at least a part of the artificial tooth structure. The base end 26 is adapted for a direct connection to the blade 10 without any intermediary elements. This connection is such that parts 32 and 34 in the bucco-lingual direction of the base 26 (FIG. 2) extend outwardly from the connection part of the blade. These extensions define a plurality of shoulders for receiving and supporting the artificial tooth structure. Also, by keeping the apex or connecting portion of the blade to the post as wide as possible there can be no weakness in the area which could otherwise cause bending or loss of bone.

Figure 2:
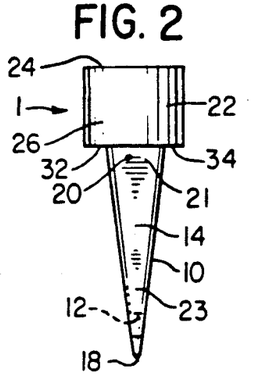
FIG. 2 is a side view of the dental implant of FIG. 1.

FIG. 2 shows that the plate 10 in the bucco-lingual plane has a wedge-shaped configuration with wide end 21 and narrow end 23. The connection part 20 of the plate is positioned at the wide end 21 of the wedge-shaped plate. Further, it can be seen that the narrow neck common to prior art devices has been eliminated. Instead, the post is even thicker than the blade over its entire length. This allows the post to resist the forces of mastication. In the view of FIG. 1 it can also be seen that the connection part 20 and the post 22 have great thickness in the mesial-distal direction so that a rigid structure in all directions is obtained.

Figure 3:
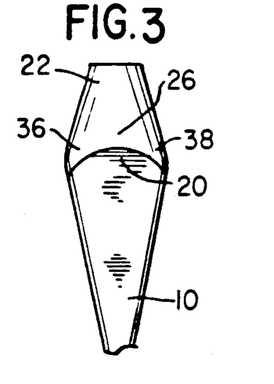
FIG. 3 is a side view of another embodiment of the dental implant.

In the embodiment of invention illustrated in FIG. 3, wings 36 and 38 of the base 26 of the post overlap a top portion of the connection part 20 in the bucco-lingual direction. This makes the transition between the post and the blade smoother, reducing even further the stresses common to the neck-type oral implants.

Figure 4:
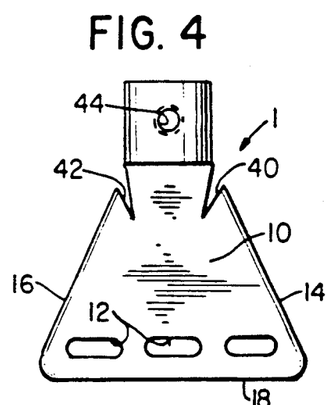
FIG. 4 is a view of still another embodiment of the dental implant.
Figure 5:
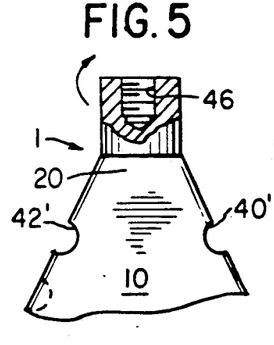
FIG. 5 is a partial view of a further embodiment of the dental implant.
Figure 6:
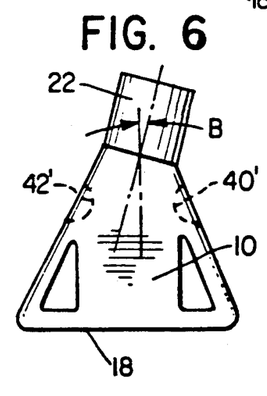
FIG. 6 is a front view of an additional embodiment of the invention.

To facilitate bending of the oral implant in the mesio-distal direction to align the artificial tooth with remaining natural teeth, a bending arrangement is provided within the blade of the invention. This bending arrangement is illustrated in FIG. 4 and includes at least two V-shaped slits or cavities 40, 42 extending from outer surfaces of the sides 14, 16 into the body of the blade. The cavities 40, 42 are positioned at an angle to and equidistantly spaced from the base 18 of the blade. However, alternative configurations of the cavities are possible. For example, FIG. 5 shows the cavities 40' and 42' having a semi-circular design. These cavities or the slits of FIG. 4 can be located at different heights on the implant. For example cavity 42' could be located at a lower point such as shown in dotted line on FIG. 5. When the post is bent in the mesial-distal direction, as shown by the arrow in FIG. 5, notch 42' tends to move upwardly and notch 40' tends to move downwardly so that the grooves tend to end up at about the same height as shown in dotted line in FIG. 6.

If, in order to align the post 22 with other teeth along the occlusal plane, an angle of inclination B (FIG. 6) of the post 22 to the blade 10 in the mesio-distal direction is needed, the implant may be bent as described. However, as an alternative, the oral implant may be manufactured by casting or otherwise with a post permanently positioned at the angle B to the blade in the mesio-distal direction. This angle may be, for example, 15°. In such a case the cavities 40', 42' shown in FIG. 6 need not be provided.

Figure 7:
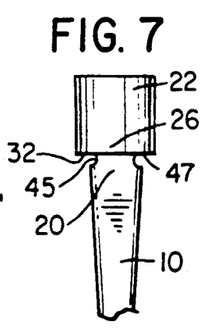
FIG. 7 is a side view of a still further embodiment of the invention.
Figure 8:
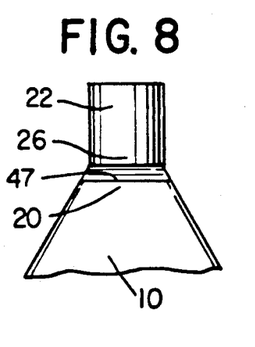
FIG. 8 is a front view of FIG. 7.

FIGS. 7 and 8 show an oral implant having a bending arrangement which facilitates bending in the bucco-lingual direction.

The bending arrangement of these figures includes two grooves 45 and 47 extending along both sides of the blade 10. The grooves are positioned at a place of connection between the second end 26 of the post and the connection part 20 of the blade.

Figure 9:
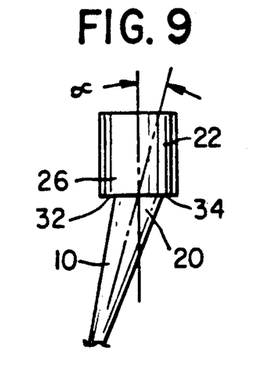
FIG. 9 is a side view of another embodiment of the invention.

An embodiment of FIG. 9 is manufactured with the post 22 positioned at an angle α to the blade 10 in the bucco-lingual direction. Similar to the embodiment of FIG. 6, the embodiment of FIG. 9 can be used when the required angle of inclination α is known in advance. Also, implants of this type can be cast with several standard offset angles for selection by the oral surgeon, e.g. 15°, 25°, etc.

Figures 10, 11, 12, 13, 14, 15, 16, 17, 18, 19:
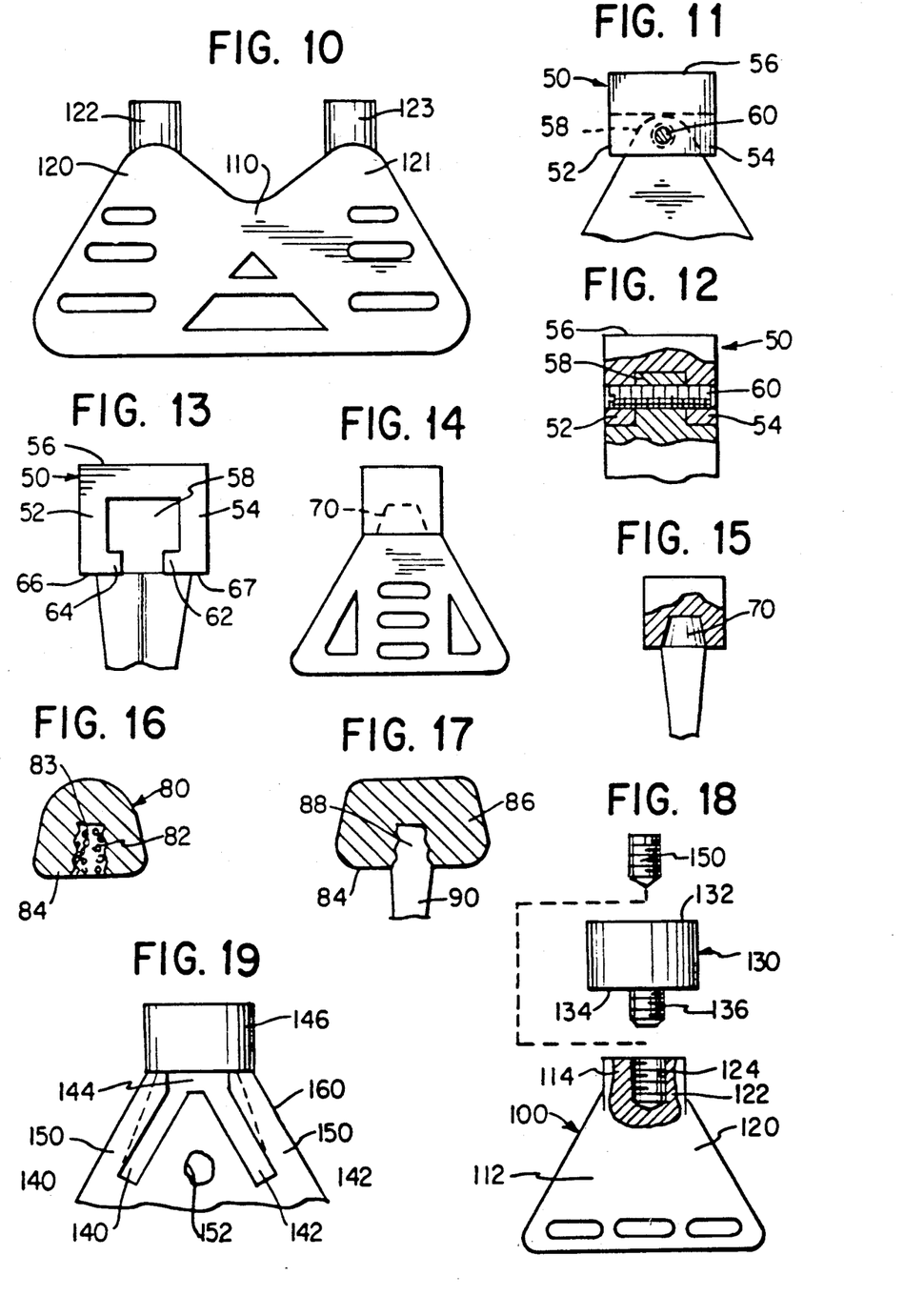
FIG. 10 is a view of the dental implant with two posts.
FIG. 11 is a partial view of a still further embodiment of the dental implant.
FIG. 12 is a side cross-sectional view of FIG. 11.
FIG. 13 is an enlarged broken view of the dental implant.
FIG. 14 is a view of a still further embodiment of the dental implant.
FIG. 15 is a side view of FIG. 14.
FIG. 16 is a cross-sectional view of one embodiment of the post.
FIG. 17 is a partially-sectional view showing a connection between the post and the blade.
FIG. 18 is a front view of a semi-submergible oral implant.
FIG. 19 is a cross section of an implant designed with legs that extend into the cortical plate and straddle the inferior alveolar nerve.

The oral implant can have one post portion, as is shown in FIG. 1, or a plurality of the posts attached to the same blade. FIG. 10, illustrates an embodiment having two post portions 122 and 123 attached to the same blade 110. There are two connection parts 120 and 121 in the blade 110, each adapted to receive the individual post portion. A plurality of the posts can be used when a better support of an artificial dental structure by the oral implant is needed, i.e. to support dental bridges etc.

The posts can be circular, oval or rectangular with tapering or non-tapering outside walls.

The crown or the bridge can be attached to the oral implant by a screw or screws which pass through an opening in the crown or bridge into either horizontal threaded holes 44 in the post as shown in FIG. 4 or vertical threaded holes 46 as shown in FIG. 5. The vertical threaded hole and the screw inserted therein can be extended to penetrate through the post into the blade.

The oral implant of the invention can be provided with post or posts removable from the blade. In that case (see FIGS. 11-13) a post 50 is provided with legs 52 and 54 projecting outwardly from the first end 56 of the post. In an assembled condition of the oral implant, the legs 52 and 54 straddle a recessed part 58 of the blade connection part. Initially it can be merely a frictional connection between the legs and the connection portion as shown in FIGS. 12 and 13. As shown in FIG. 13 the legs can have inward projections 62 and 64 that snap into grooves in the connection portion.

To provide a fixed connection between the post and the blade, a screw 60 (FIGS. 11 and 12) can be used. This screw passes through threaded openings in the legs 52 and 54 of the post and a threaded opening in the recessed part 58 of the connection portion.

FIG. 13 further shows that legs 52 and 54 are made wider than the connection part of the blade, thus providing bucco-lingual shoulders 66, 67 for support of the artificial tooth structure.

The embodiment of FIGS. 11-13 may be made similar to the embodiment of FIG. 3, in that the lower parts of the legs (not shown in the drawings) can be extended to overlap the top portion of the connection part in the bucco-lingual direction.

FIGS. 14 and 15 illustrates an alternative to the design of FIGS. 11-13 in which each leg of the post may fit within recesses in the connection part of the blade, so that the substantially flat outside surfaces of the legs fit flush with the buccal and lingual surfaces of the blade.

The post shown in FIGS. 14 and 15 does not have legs for engagement with the connection part of the blade. Instead, a cavity 70 is arranged in the central area of the second end of the post. The cavity 70 extends from an outer surface of the base of the post and is adapted to closely receive the connection part of the blade. A vertical or horizontal screw can be used to fixedly attach the post to the blade.

The oral implant of the invention can be installed by first making an incision in the fibromucosal tissue down to the underlying bone. The tissue is reflected and a groove is drilled in the bone using a burr. This groove is made about the width of the base of the blade. The blade can then be snugly fit therein in such a manner that at least a portion of the connection part of the blade extends beyond the plane of the bone. In some instances, the connection part can be positioned just below the rim of the opening in the bone, allowing the second end of the overlapping post to rest on the bone. Once the blade is in place, the tissue is sutured over the blade. Several weeks or months are allowed to pass before the dental prosthesis is attached to the post. During this period, the bone starts to grow around the implant portion and through the holes provided in it until surrounding bone becomes integrated with the blade. This is necessary to anchor the implant in place before it is stressed by use.

If a unitary blade and post are used, the next step is to install the artificial tooth structure on the post. If a separable post is used, the post must be attached to the connection part, e.g. by screws, before the prosthesis is installed.

The use of screws and similar devices for attachment of a post to a blade requires additional space for drilling of threaded holes in these elements of the implant. Placement of such a threaded connection can be time consuming and not always reliable. The present invention offers a new way of connecting the blade and the post which allows the oral surgeon to avoid the above disadvantages of the threaded connections.

In FIGS. 16 and 17, there is shown a post 80 with an inside cavity 82 that extends from an outer surface 84 of the base end 86 into its body. The cavity is designed for close engagement with the connection part 88 of a blade 90. At least the connection part 88 of the blade is made from a material softer than the material of the post.

A plurality of tiny rigid bubbles or rigid three dimensional raisings extend outwardly and inwardly from a surface of the cavity 83. One or more rough areas are thus defined by the bubbles within the surface 83. These bubbles can be created during the process of casting the post or may be etched therein.

The post can be connected to the blade by positioning the cavity of the post over the end of the connection part 88. A mallet or similar tool may be used to force the cavity 83 of the post onto the connection part 88 of the blade. As a result, the rigid bubbles of the post are crushed as the cavity is penetrated deeply by the connection part of the blade. This results in a cold weld locking of the two pieces together.

The various parts of each of the embodiments may be made of titanium, vitalism or surgical stainless steel. In the case of the embodiment of FIGS. 16 and 17, the relative hardness of these materials should be considered in selecting the materials and typically the post and blade would be made of different materials.

A truly submergible dental implant 100 is shown in FIG. 18. This implant includes an implant portion 112 and a post portion 130 which are manufactured as two separate pieces. A connection part 120 of the implant portion is positioned at a place of connection between the implant portion and the post portion. The connection part 120 has a receiving element 122 for receiving at least a part of the post. The receiving element 122 extends outwardly from the implant portion in the direction of the occlusal plane for a short distance, e.g. 2-3 mm.

The post portion 130 has a first end 132 and a second or base end 134. The first end receives at least a part of the artificial tooth structure. The base end 134 is adapted for a direct engagement with the receiving element of the implant portion. The receiving element 122 has the lateral dimension as wide as the lateral dimension of the base end 134 of the post.

A fastening member 136 protrudes outwardly from the base end 134. The receiving element 122 has an opening 124 for receiving the fastening member 136. In the embodiment of FIG. 18 the fastening member 136 and the opening 124 have threads for mutual engagement.

The opening 124 is also adapted to receive a cap or plug 150. The plug is designed to be threaded into the opening for closing thereof. The plug and the implant can be made from the same material, i.e. titanium, vitalium or surgical stainless steel. As an alternative the plug can also be made of Teflon or another suitable plastic.

The implant of FIG. 18 is installed in a manner similar to the above discussed. However, a groove is drilled in the bone deep enough for the implant portion 110 to be submerged in the groove below its upper rim in such a manner that only the receiving element 122 of the connection part 120 protrudes outwardly from the groove in the direction of the occlusal plane.

However, element 122 is so short it does not extend above the gum tissue. Once the implant portion is in place, the plug 150 is threaded into the opening 124. The gum tissue is then sutured over the implant portion and the receiving element. As a result, only a very small part of the implant portion protrudes above the tissue. Thus the implant is protected from impact with the patient's tongue and other teeth.

During the waiting period the surrounding bone and tissue became integrated with the implant portion. However, the plug 150 prevents tissue growth in the opening 124.

Once the dentist is sure that the implant portion is firmly anchored in the bone, a new incision is made in the tissue and the plug is removed. In place of the cap, the post 130 is threaded into the opening 124.

When a patient's alveolar ridge bone 160 is wide, a groove can be made across the ridge bucco-lingually or labio-platally so as to span the soft medullary bone and include the tougher cortical bone near the surface of the ridge. In such a case the blade can be made with a cross section like that in FIG. 19. The blade of FIG. 19 has buccal and lingual legs 140, 142 connected by a transverse connection part 144 upon which post 146 is located. As shown, the outer edges of the legs are received in the cortical plate 150 but circumvent the inferior alveolar nerves 152 by straddling them. In this manner the implant can take advantage of the maximum available bone by extending into the area near or in the cortical bone, while avoiding the nerves.

The shape of the side of the implant of FIG. 19 may be like any of the other designs in this application or in common use. Also the cross-sectional shape may be modified in any convenient manner to conform to existing bone and nerve conditions. For example the legs may be parallel and vertical, instead of slanted toward each other as in FIG. 19. Also, the legs may slant away from each other and the portions surrounding the nerve may form a smooth curve. In determining which shapes to use or fashion, CAT scans and tomograms may be used to locate the nerve and to define the bone structures.

As with the other implants discussed, the implant of FIG. 19 may be made submergible by making the post detachable from the blade.

Figures 20, 21, 22:
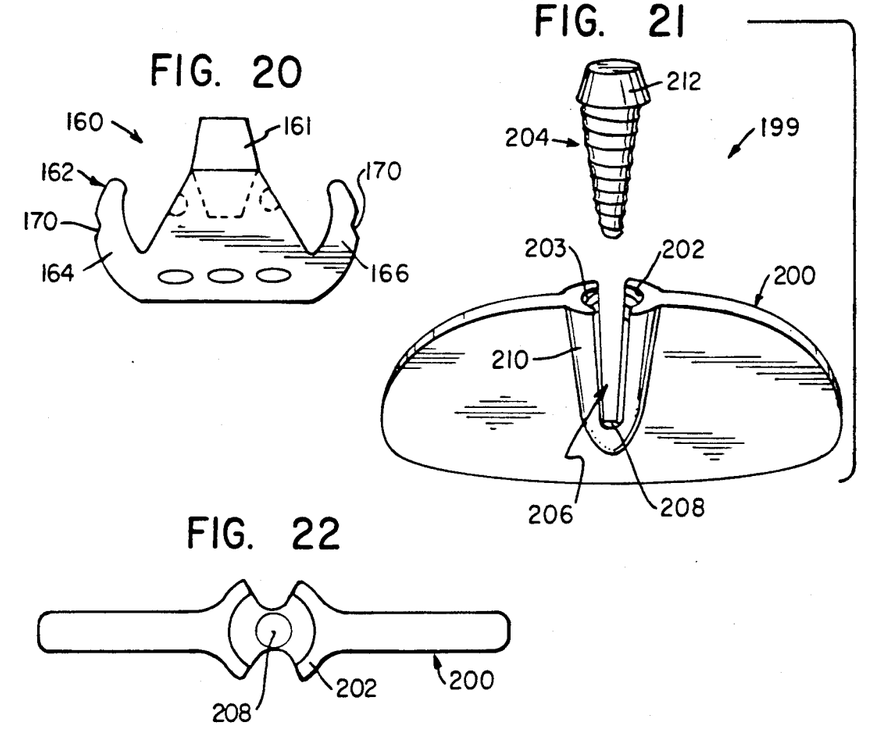
FIG. 20 is a front view of a still further embodiment of the dental implant.
FIG. 21 is a perspective view of a further embodiment of the dental implant.
FIG. 22 is a top view of the blade portion of the dental implant of FIG. 21.

FIG. 20 shows another embodiment of the present invention. The dental implant 160 has an implant portion 162 which has mesial and distal occlusional struts 164, 166 extending upwardly from the sloping shoulders. These struts 164, 166 terminate approximately 2 mm below the level of the mounting post 168 in the buccal and lingual cortices of bone. This allows a portion of the struts 164, 166 to terminate within the strong cortical bone which lies close to the gum. The cortical bone is stronger than the medullary bone which lies deeper within the jaw. The additional implant surface area surrounded by the cortical bone creates a stronger anchor within the jaw. The struts 164, 166 may have slots 170, which allow them to be grasped by dental tools for insertion and/or bending as needed.

The implant of FIG. 20 can be made submerigible if the post 168 is made detachable from the body 162. The connection between them, shown in dotted line in FIG. 20, may be by any convenient means, e.g. the arrangement of FIGS. 21-25. It may also be provided with recesses on either side of the point of connection (also shown in dotted line in FIG. 20) which are like the recesses 40', 42' of FIG. 5.

FIG. 21 shows a still further embodiment of the present invention. This arrangement provides the benefits of both a blade and a screw-type dental implant. With this implant 199 a blade body 200 is provided. This blade body has a generally inverted triangular shape, but may be in any other convenient shape. At a position along the upper surface of the blade there is a 360° coronal ring or collar 202. If desired, this ring or collar may have internal threads which match the threads 203 of a screw post 204. As shown more clearly in FIG. 22, the coronal ring 202 extends beyond the lateral walls of the blade portion. Below the coronal ring there is a cavity 206 in the blade body which terminates at its lower end in an apical disc or concavity 208.

In the implant of FIGS. 21 and 22, the body of the blade 200 has a bulge 210 at the location where the screw 204 engages the threaded cavity 206 in the blade. Portions of the bulge 210 are removed so that the threads of screw 204 extend into the flanking bone and provide a secure anchoring of the blade and screw in the bone. This body bulge 210 gives support and guidance to the screw 204.

In any of the arrangements shown with detachable posts, the post can be arranged such that it does not rest on the top surface of the blade and there is a small amount of neck available. This may aid in attaching the artificial tooth to the post. The increased strength of the neck, as shown in the arrangments of the previous figures, permits the use of a small neck without significantly weakening the overall implant. However, when the post rests on the upper surface of the shoulder of the blade, there is increased lateral support for the post.

The screw 204 has a connected post 212 to which the artificial tooth will be attached. Thus, once the screw 204 is in place, it never has to be removed. The connected post 212 shown in FIG. 21 is of the basket type, but it could also have male or female threads for receiving a threaded tooth.

Figure 23:
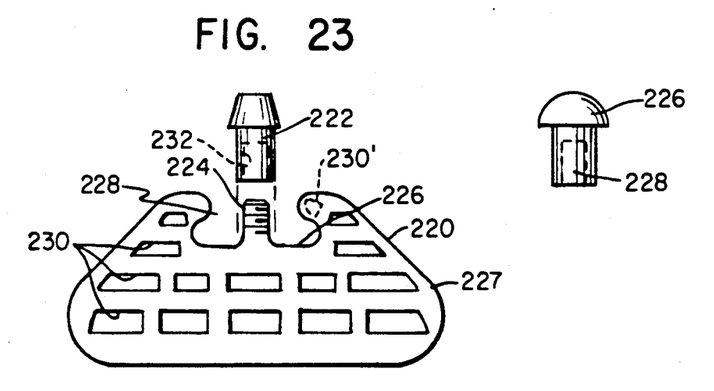
FIG. 23 is a front view of a still further embodiment of the dental plant.

FIG. 23 is a further example of a submergible blade 220 without a weak neck part on its detachable post 222. The post 222 is connectible to a connection part 224, which is in the form of a projection with a threaded cavity at its end. In cross section the blade 220 may be an inverted triangular shape, tapered or some other suitable shape.

The connection part 224 extends toward the occlusal plane from the bottom surface 226 of a recess 228 in the blade. The end of this projection is at about the level of the upper or superior surface 227 of the blade. As a result, when the blade 220 is buried in the bone, either no part of the connection part 224 or very little sticks out of the hole in the bone. This allows the gum tissue to be placed over the projection, even after a plastic cap 226 is secured over the projection.

The plastic cap 226 has a cavity 228 which allows it to seat well down on the projection. The cavity may have threads which match those of projection 224. Thus, the cap can be threaded onto the projection. Alternatively, if the cap 226 is flexible, it may not have threads in the cavity and may merely be pushed down over the projection.

When the gum tissue is sutured in place over the blade and cap, they remain in place while new bone grows over the top of the blade, except where the cap is located, and through the parallel rows of vents 230 which extend at least part way through the blade. While not necessary, the vents in FIG. 23 are shown to be of substantially equal size and equally spaced. Other arrangements are also possible, e.g., vents 230' (in dotted line) may be made to conform to the area of the blade near the post.

When healing is complete, bone has grown all around the blade and into the recess 228 and vents 230, except where the cap is located. This bone even covers the undercut region of the recess 228 near the surface 226.

At this point, the tissue is opened and the cap is removed and replaced with the post 222, which post may have a threaded cavity 232 for attachment to connection part 224. This post is long enough to stick up out of the gum and provide a mounting surface for an artificial tooth or bridge.

The base surface 226 is very broad and is at least as wide as the blade. Thus, it provides a strong support for the post 222. The connection part 224 may even be wider than the blade so that the post and projection are very strong and form a bulge in the overall implant at the site of the post.

While only one post 222 and connection part 224 are shown in the embodiment of FIG. 23, it should be understood that two or more may be provided on a single blade. Also, the distance between the connection part 224 and the edge of recess 228 may be different, but a distance of about 15 mm is preferred. The depth of the recess 228 may also be varied as suitable.

An inverted triangular blade is shown in FIG. 23. However, this invention may be utilized with blades of various shapes.

What is claimed is:

1. An oral implant for supporting an artificial tooth structure, comprising:
   an implant portion having a top surface and a connection part located along the top surface, the connection part defining an area on the top surface having sides and generally orthogonal ends, the distance between the sides of the connection part being as wide as the lateral dimension of the rest of the implant portion, the implant portion being adapted to be fitted in an opening in a bone in the vicinity of the occlusal plane of a patient in such a manner that at least a part of the connection part extends beyond the rim of the opening in the bone or remains just below it and is directed toward a base of the opening away from the rim, the implant portion having a substantially triangular configuration, the connection part of the implant portion being positioned at the apex of the triangle, the implant portion having mesial and distal occlusional struts extending from the sides of the implant portion, said struts directed toward a plane perpendicular to the triangle apex and terminating in an area of bucco-lingual cortice of bone when installed in a patient; and
   at least one post portion having first and second ends, the first end being adapted to receive at least a part of said artificial tooth structure and the second end being adapted for a direct connection to the connection part of the implant portion, the post portion having lateral dimensions such that a part of the second end extends outwardly at least to the sides of the connection part and defines shoulders for supporting the artificial tooth structure, the shoulders of the second end of the post portion extend outwardly from sides of the triangle, and the post portion having longitudinal dimensions such that another part of said second end extends outwardly at least to the ends of said connection part, the implant portion having bucco-lingual side surfaces in the mesio-distal plane connected with the top surface along a connection edge, the connection edge sloping toward the base of the opening in the direction away from the connection part so that the top surface in the direction away from the connection part is substantially below the rim, whereby bone may grow over the implant portion up to the connection part and no narrow neck portion is provided between the post portion and the implant portion.

2. An oral implant according to claim 1, wherein the shoulders of the second end overlap surfaces of the connection part of the implant portion extending in the bucco-lingual direction.

3. An oral implant according to claim 1, wherein the shoulders to the second end extend in the bucco-lingual direction.

4. An oral implant according to claim 1, wherein a cross-section of the implant portion in the bucco-lingual direction has a wedge-shaped configuration with wide and narrow ends, the wide end being connected to the second end of the post portion.

5. An oral implant according to claim 1, wherein the implant portion further comprises bending means to enable the oral implant to bend in the mesio-distal direction, the bending means being located within the implant portion and spaced from the connection part.

6. An oral implant according to claim 5, wherein the bending means comprises at least one cavity extending into a side of the implant portion.

7. An oral implant according to claim 1, wherein the first end of the post portion has receiving means for receiving a fastener for fastening the artificial tooth structure to the post portion.

8. An implant according to claim 1, wherein each of the struts includes a slot to facilitate handling with dental tools.

9. An oral implant according to claim 1, wherein a plurality of post portions are attached to the implant portion.

10. An oral implant according to claim 1, wherein the post portion is detachably connected to the implant portion and the second end of the post portion is adapted to straddle the connection part of the implant portion when connected thereto.

11. An oral implant according to claim 10, wherein at least one fastening means is provided for fastening the post portion to the implant portion.

12. An oral implant for supporting an artificial tooth structure, comprising:

an implant portion adapted to be fitted in an opening in the bone of a patient in the vicinity of the occlusal plane, said implant portion having an upper surface directed toward the occlusal plane when the implant portion is installed in the opening, the implant portion having a substantially triangular configuration, an area of the upper surface of the implant portion being positioned at the apex of the triangle, the implant portion having a cutout extending from side to side and from the area of the upper surface of the implant portion positioned at the apex of the triangle toward a base of the implant portion; and a post having a shaft extending from one end, the shaft having a diameter larger than the lateral dimension of the implant portion, the shaft being adapted to be inserted into the cutout and to come into engagement with the bone flanking the cutout;

the implant portion having bucco-lingual side surfaces in the mesio-distal plane connected with the upper surface along a connection edge, the connection edge sloping toward the base of the implant portion in the direction away from the post such that the upper surface in the direction away from the post is substantially below the rim of the opening, whereby bone may grow over the apex of the triangle up to the post and no narrow neck portion is provided between the post and the implant portion.

13. An oral implant according to claim 12, wherein the lateral dimensions of the post are at least substantially as great as the lateral dimensions of the implant portion at the upper surface.

14. An oral implant according to claim 12, wherein the shaft is threaded, and the cut out is provided with threads that mate with the threads of the post shaft.

15. An oral implant according to claim 12, further including a coronal ring at the upper surface where the cut out is located in order to receive and guide the shaft.

16. An oral implant according to claim 15, wherein the shaft is threaded, and the coronal ring has threads that mate with the threads of the shaft.

17. An oral implant according to claim 12, wherein the base of the cut out has an apical disc to receive the end of the shaft and to guide it in place.

18. An oral implant according to claim 12, wherein the shaft is threaded, the cut out is provided with threads, and further including an apical disc at the base of the cut out and a threaded coronal ring at the location along the upper surface where the cut out ends, the threads of the cut out and the coronal ring mating with the threads of the shaft.

19. An oral implant according to claim 12, wherein the post is detachable from the shaft and further includes means for fastening the shaft to the post.

20. An oral implant according to claim 19, wherein the lateral dimensions of the post are at least as great as the lateral dimensions of the upper surface of the implant portion.

21. An oral implant according to claim 12, wherein the implant portion has a lateral bulge at the location of the cut out, the bulge extending no higher than the apex of the triangle.

22. An oral implant according to claim 12, wherein the post has a connecting part for receiving the artificial tooth structure.

23. An oral implant for supporting an artificial tooth structure, comprising:

an implant portion adapted to be fitted in an opening in the bone of a patient in the vicinity of the occlusal plane such that it is submerged below the rim of the opening, said implant portion having an upper surface directed toward the occlusal plane when the implant portion is installed in the opening, the implant portion having a substantially triangular configuration with an apex and a base, an area of the upper surface of the implant portion being positioned at the apex of the triangle, the implant portion having a recess extending from side to side and from the upper surface of the implant portion;

the implant portion including a connection part in the form of a projection from a base surface of the recess extending no higher than said upper surface; and a post having a shaft extending from one end, the shaft being connectable to said connection part projection;

the implant portion having bucco-lingual side surfaces in the mesio-distal plane connected with the upper surface along a connection edge, the connection edge sloping toward the base of the implant portion in the direction away from the connection part such that the upper surface in the direction away from the connection part is substantially below the rim of the opening, whereby bone may grow over the apex of the triangle up to the connection part and no narrow neck portion is provided between the implant portion and the connection part.

24. An oral implant according to claim 23, wherein the shaft of the post has external threads and the connection part projection has a cavity with mating internal threads such that the post may be connected to the connection part via the mating threads.

25. An oral implant according to claim 23, wherein the shaft of the post has a cavity with internal threads and the connection part projection has external mating threads such that the post may be connected to the connection part via the mating threads.

* * * * *